(12) United States Patent
Benchikh et al.

(10) Patent No.: US 8,906,633 B2
(45) Date of Patent: Dec. 9, 2014

(54) DETECTION OF SYNTHETIC CANNABINOIDS

(75) Inventors: Elouard Benchikh, Crumlin (GB); Stephen Peter Fitzgerald, Crumlin (GB); Paul John Innocenzi, Crumlin (GB); Philip Andrew Lowry, Crumlin (GB); Ivan Robert McConnell, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 11 days.

(21) Appl. No.: 13/332,042

(22) Filed: Dec. 20, 2011

(65) Prior Publication Data

US 2012/0208213 A1 Aug. 16, 2012

(30) Foreign Application Priority Data

Feb. 14, 2011 (GB) .................................. 1102544.2
Jun. 21, 2011 (GB) .................................. 1110425.4

(51) Int. Cl.
*G01N 33/53* (2006.01)
*C07K 14/435* (2006.01)
*C07K 17/14* (2006.01)

(52) U.S. Cl.
CPC ................ *C07K 17/14* (2013.01); *Y10S 435/81* (2013.01)
USPC ........... 435/7.1; 435/7.92; 435/810; 436/501; 530/363; 530/389.1; 530/389.3; 530/395; 530/400

(58) Field of Classification Search
None
See application file for complete search history.

(56) References Cited

U.S. PATENT DOCUMENTS

| | | | | |
|---|---|---|---|---|
| 5,817,766 A * | 10/1998 | Hui et al. | .................... | 530/387.1 |
| 6,900,236 B1 | 5/2005 | Makriyannis et al. | | |
| 2013/0066053 A1* | 3/2013 | Fitzberald et al. | ......... | 530/389.8 |
| 2013/0196354 A1* | 8/2013 | Fitzgerald et al. | ........... | 435/7.92 |

FOREIGN PATENT DOCUMENTS

| | | |
|---|---|---|
| EP | 0736529 A1 | 10/1996 |
| WO | 02073214 A2 | 9/2002 |
| WO | 2010127452 A1 | 11/2010 |

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Kraemer, T., "V10—Studies on the metabolism of JWH-18, the pharmacologically active ingredient of different misused incenses," Abstracts—Vortrage Hauptsymposium, (2008), vol. 76, No. 2, pp. 90.
Sumandeep, R., et al., "Routine Screening of Human Urine for Synthetic Cannabinoids by LC-MS/MS Utilizing Spectrum Based Library Search," Redwood Toxicology Laboratory, Soft 2010. (Abstract).
Uchiyama, N., et al., "Chemical analysis of synthetic cannabinoids as designer drugs in herbal products," Forensic Science International, (2010), vol. 198, pp. 31-38.
Dresen, S., et al., "Monitoring of herbal mixtures potentially containing synthetic cannabinoids as psychoactive compounds," J. Mass. Spectrometry, (2010), vol. 45, pp. 1186-1194.
Hudson, S., et al., "Use of High-Resolution Accurate Mass Spectrometry to Detect Reported and Previously Unreported Cannabinomimetics in "Herbal High" Products," pp. 252-260, J.Anal. Toxicol., 2010, v.34.
Moller, I., et al., "Screening for the synthetic cannabinoid JWH-018 and its major metabolites in human doping controls," Drug Testing and Analysis, (2010), pp. 609-620.
Sobolevsky, T., "Detection of JWH-018 metabolites in smoking mixture post-administration urine," Forensic Science International, (2010), vol. 200, pp. 141-147.
Wintermeyer, A., et al., "In vitro phase I metabolism of the synthetic cannabimimetic JWH-018," Anal. Bioanal. Chem. (2010), vol. 398, pp. 2141-2153.
Liu, Y., et al., "Design and synthesis of AX4697, a bisindolylmaleimide exo-affinity probe that labels protein kinase C alpha and beta," Bioorganic & Medicinal Chemistry Letters, (2008), vol. 18, pp. 5955-5958.
Salamone, S., et al., "A Non-Cannabinoid Immunogen Used to Elicit Antibodies with Broad Cross-Reactivity to Cannabinoid Metabolites," J. Forensic Sciences, (1998), 43(4), pp. 821-826.
Singh, P., et al., "Synthesis and evaluation of indole-based new scaffolds for antimicrobial activities—Identification of promising candidates," Bioorganic & Medicinal Chemistry Letters, (2011), vol. 21, pp. 3367-3372.
Huffman, J., et al., "1-Pentyl-3-phenylacetylindoles, a new class of cannabimimetic indoles," Bioorganic & Medicinal Chemistry Letters, (2005), vol. 15, pp. 4110-4113.

* cited by examiner

*Primary Examiner* — Galina Yakoleva
(74) *Attorney, Agent, or Firm* — Saul Ewing LLP; Kathryn Doyle; Domingos J. Silva

(57) ABSTRACT

The invention describes methods and kits for detecting and determining current and future synthetic cannabinoids from the JWH and CP families. Unique antibodies derived from novel immunogens enable said methods and kits.

11 Claims, 8 Drawing Sheets

DETECTION OF SYNTHETIC CANNABINOIDS

BACKGROUND

The increasing rise in the use of stealth drugs (novel synthetic drugs that were previously or remain analytically/structurally uncharacterised and unclassified by government institutions), is exemplified by synthetic cannabinoid products which incorporate JWH-018 and/or CP 47,497 as the active ingredient. Stealth synthetic cannabinoid (SSC) drug manufacturers can base their choice of active molecular target on scientific literature studies that address the therapeutic potential of CB1 (the CNS cannabinoid receptor) agonists and antagonists. By incorporating novel, analytically uncharacterised compounds with high CB1 receptor affinity into herbal mixtures (packaged under such names as Spice, Yucatan Fire) the manufacturers are able to legally target drug consumers clandestinely by promoting the material as herbal therapeutics. A problem for governments and drug enforcement agencies is that even after identifying and banning a new synthetic cannabinoid, the manufacturers can rapidly react to the banning by incorporating a different active analogue into the same or a different herbal product; targeted minor changes in the molecular structure of the known active compound can preserve receptor activity but often produces a molecule whose GC-MS/LC-MS (the commonly applied detection techniques) profile is completely different from the original active molecule. Hence the new active molecule initially remains unidentified and a further resource intensive and costly chemical analytical study to enable structural characterisation is required. The main active ingredients highlighted in SSC products to date are JWH-018, CP 47,497 and JWH-073 (Uchiyama et al. 2010; Hudson et al. 2010; Dresen et al. 2010). Initial studies of the metabolism of JWH and CP compounds have highlighted metabolic processes similar to tetrahydrocannabinol (THC) metabolism, namely ring and alkyl substituent hydroxylation, carboxylation and glucuronidation. As described herein, unless otherwise stated, JWH refers to molecules comprising structure I which are CB1-active or metabolites of the CB1-active parent, in which the indole ring system is present as a fused heterobicyclic i.e. it is not part of, for example, a fused heterotricyclic ring system. Y can be hydrogen or a substituted or unsubstituted alkyl group such as butyl, pentyl or 2-(morpholin-4-yl)ethyl, while R is a carbon atom which may be part of a fused or unfused, substituted or unsubstituted aromatic ring or a substituted or unsubstituted alkyl, alkenyl or alkynyl chain optionally attached to a fused or unfused, substituted or unsubstituted aromatic ring, but is usually a substituted or unsubstituted naphthyl ring.

CP refers to synthetic cannabinoid molecules comprising the unfused bicyclic structure II, in which X is either ethyl, n-propyl or n-butyl as well as metabolites thereof.

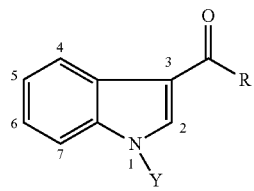

Structure I

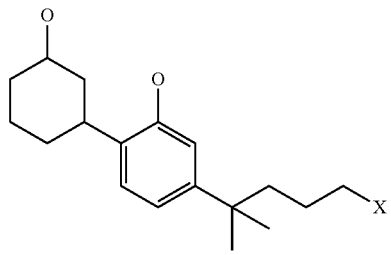

Structure II

Indolyl, naphthyl, carboxyalkyl, N-dealkylated and N-alkyl mono-, di-, and tri-hydroxylated metabolites, as well as their glucuronidated conjugates are reported JWH-018 metabolites (Sobolevsky et al. 2010; Kraemer et al. 2008). Moller et al. (2010) highlighted the same metabolites as Sobolevsky et al. (2010), with the monohydroxylated N-alkyl chain being the most abundant phase I metabolite; Wintermeyer et al. (2010) conducted an in vitro study that largely confirmed previous findings. Herbal therapeutics have been analysed using solvent extraction, pre-derivatisation and finally GC-MS analysis in SIM mode (Rana et al. 2010). This method is inadequate for the detection of future and 'current' JWH and CP SSCs (it is conceivable that 'current' herbal therapeutics, as well as JWH-018 and CP 47,497, incorporate JWH and CP SSCs that are not yet characterised), requires sample pre-derivatisation, specialist staff for its implementation and expensive equipment. In order to address the problem associated with the cheap and rapid detection of known JWH and CP molecules and their metabolites and/or future and associated metabolites based on the JWH and CP drug families, the Inventors devised a novel method based on novel antibodies raised from novel immunogens. The antibodies underpin an effective analytical and economic solution to the detection and quantification of current and future JWH and CP CB1-active molecules in in vitro patient samples and herbal therapeutics.

SUMMARY OF THE INVENTION

The invention describes a rapid and practical method for the detection and determination of known and/or stealth synthetic cannabinoids based on the JWH and CP drug families. Kits and their use for JWH and CP SSC detection and determination in herbal therapeutics and in vitro patient samples are also described. The invention is underpinned by novel immunogens and antibodies which enable said methods, kits and applications.

DETAILED DESCRIPTION OF THE INVENTION

Figure 1:
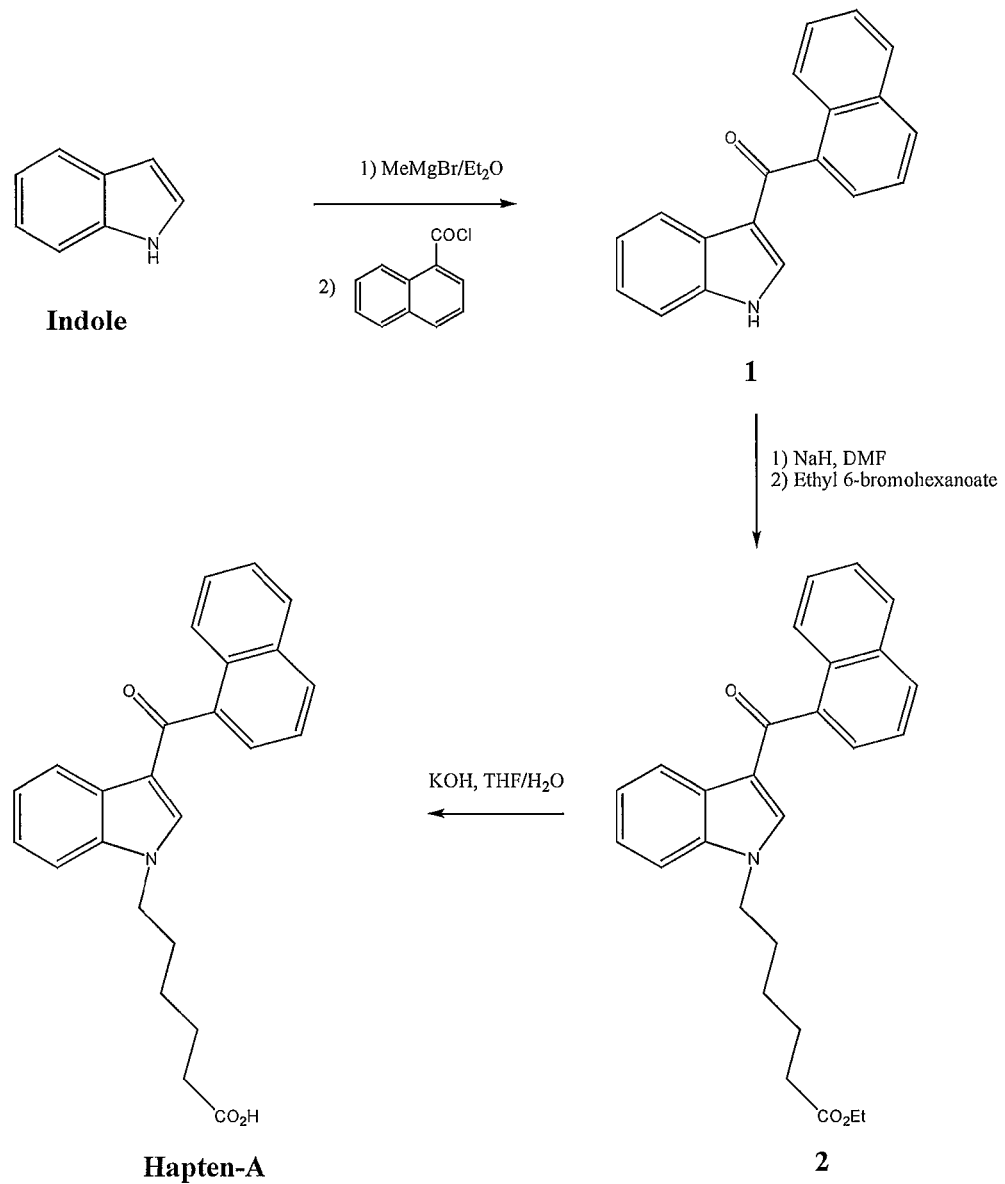
FIG. 1 is a diagram showing the synthesis of Hapten-A.
Figure 2:
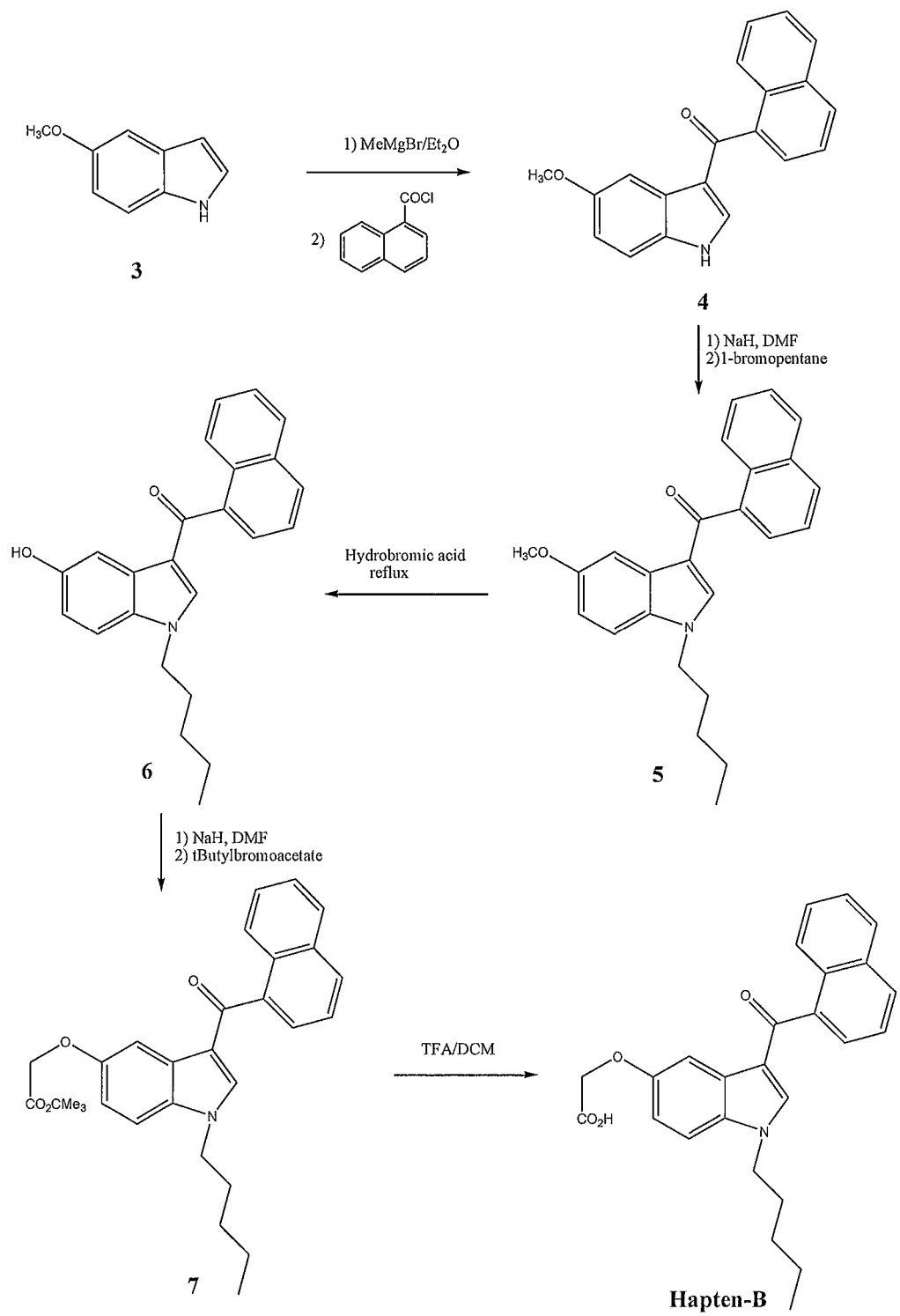
FIG. 2 is a diagram showing the synthesis of Hapten-B.
Figure 3:
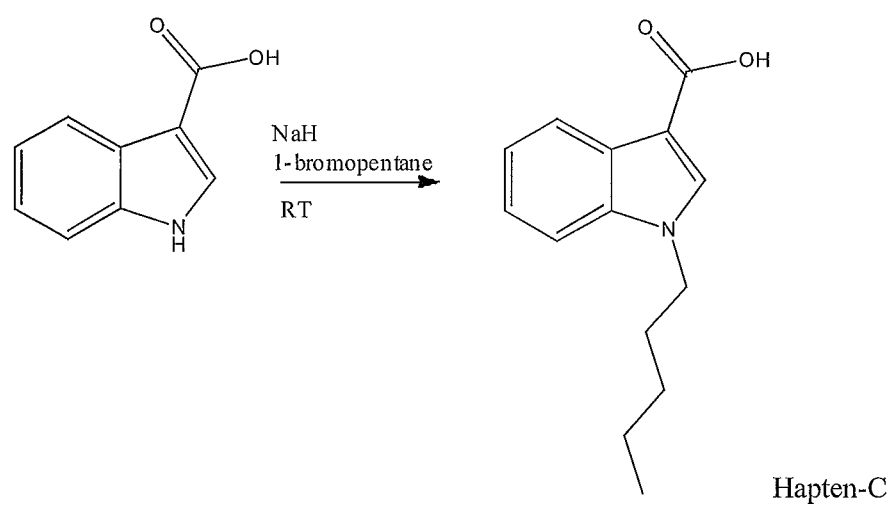
FIG. 3 is a diagram showing the synthesis of Hapten-C.
Figure 4:
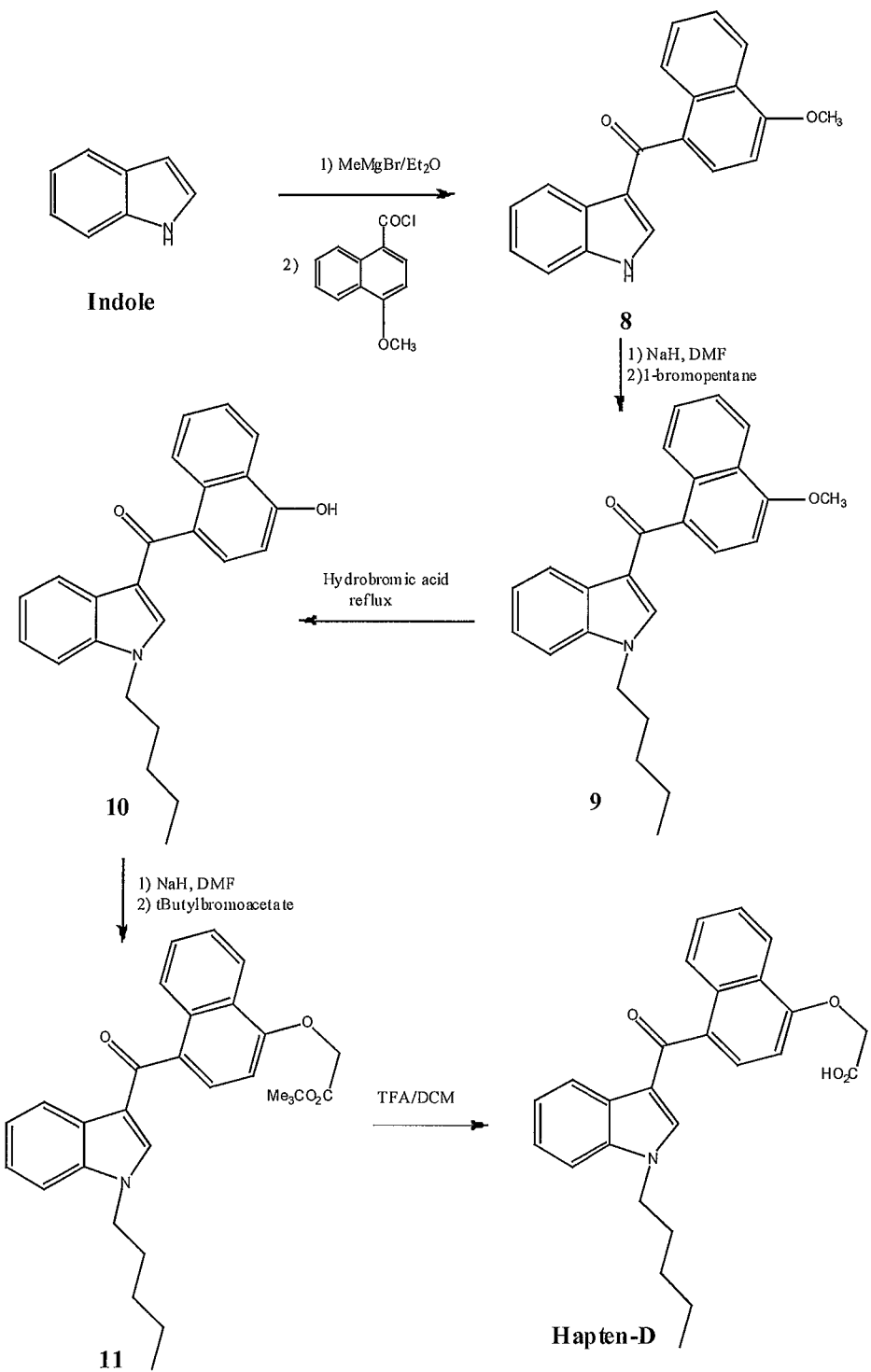
FIG. 4 is a diagram showing the synthesis of Hapten-D.

A first aspect of the invention is one or more immunogens possessing the following structures Group I (a)-(d) (immunogens of the JWH family)

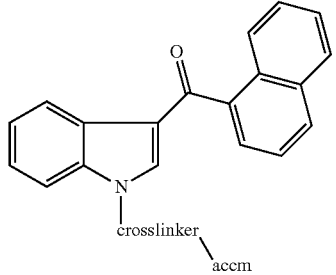
(a)

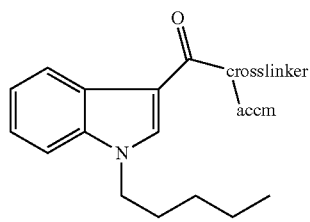
(b)

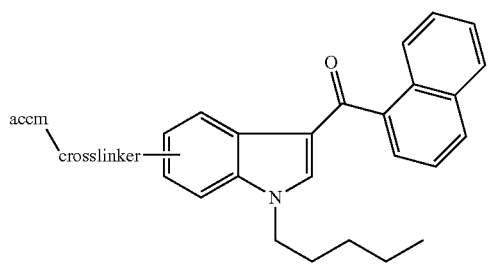
(c)

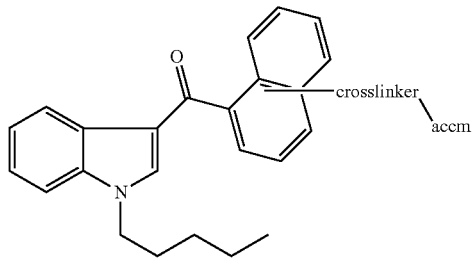
(d)

Group II (e)-(h) (immunogens of the CP family)

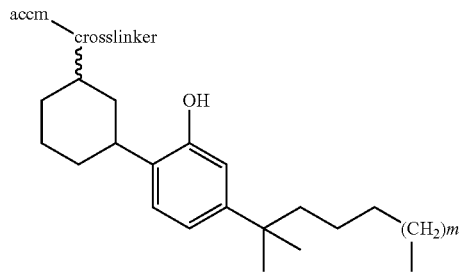
(e)

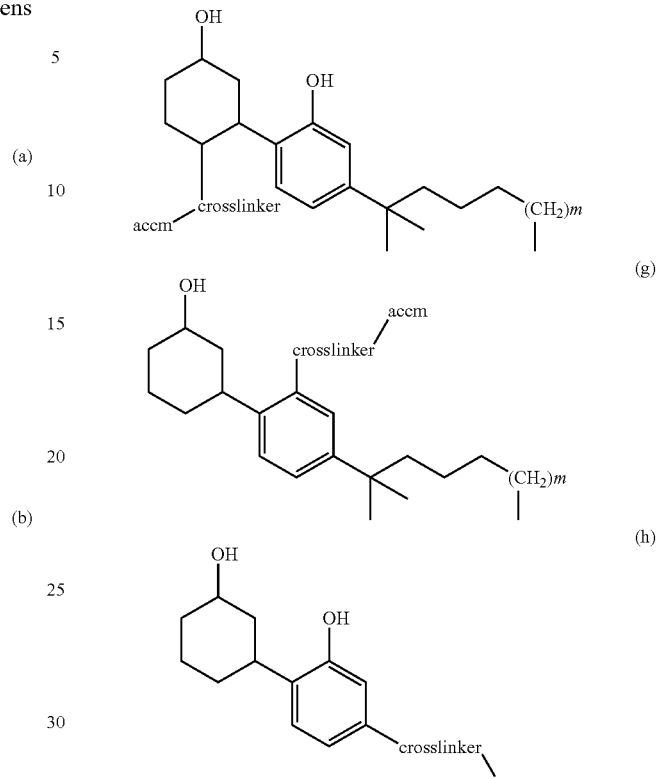

in which the accm is an antigenicity conferring carrier material; the crosslinker is a functionalised linking group joining the accm to the remainder of the molecule.

By functionalised it is meant the crosslinker incorporates atoms that enable it to bond to both the accm and the JWH or CP moiety, forming a bridging group. In structure (e) the crosslinker forms either a single or double bond to the cyclohexyl ring, in structure (c) the crosslinker extends from the 4, 5, 6 or 7-position of the indole ring and in structure (d) the crosslinker extends from the 2, 3, 4, 5, 6, 7, or 8-position of the naphthyl ring. The crosslinker concept is well known to the person skilled in immunogen synthesis. For the current invention, when conjugating the hapten to the accm to form the immunogen, the nature and length of the crosslinker follows standard methods in order to optimise hapten epitopic recognition by the antibody. This entails a crosslinker of low immunogenicity and a chain length preferably of no greater than about ten atoms, most preferably no greater than six atoms.

Preferably for structure (a) the crosslinker is —(CO)n-D-Y— and where n=0 or 1, and D is a C1-10, preferably a C1-5 substituted or unsubstituted straight chain alkylene or arylene moiety and Y, which is attached to the accm, is selected from groups such as carbonyl, amino, thiol, maleimide, isocyanato, isothiocyanato, aldehyde, diazo and dithiopyridyl. Y is preferably carbonyl or amino.

Preferably for structures (b), (c), (d), (f) and (h) the crosslinker is -(A)n-D-Y— where A=O, —N(R)—, —S—, —S(O)— (sulphoxide) or —S(O)2-(sulphonyl) and R=H or C1-5 alkyl, n=0 or 1 and D is a C1-10, preferably a C1-5 substituted or unsubstituted straight chain alkylene or arylene moiety and Y, which is attached to the accm, is selected from groups such as carbonyl, amino, thiol, maleimide, isocyanato, isothiocyanato, aldehyde, diazo and dithiopyridyl. Y is preferably carbonyl or amino.

Preferably for structure (e) m=1-3, the crosslinker is either -(L)p-M-Q- or =N—O-M-Q- in which Q, attached to the accm, is either carbonyl or amino, M is a C1-10, preferably a C1-5 substituted or unsubstituted straight chain alkylene or arylene moiety, p=0 or 1 and L is O, NH, S, ester, thioester, or amide.

Preferably for structure (g) m=1-3, the crosslinker is -(L) p-M-N— in which N, attached to the accm, is either carbonyl or amino, M is a C1-10, preferably a C1-5 substituted or unsubstituted straight chain alkylene or arylene moiety, p=0 or 1 and L is O, NH, S, ester, thioester, or amide.

Preferred immunogens correspond to structures (a) and (c). The crosslinker of structure (c) of Group I is preferably attached to the 5-indole position. The crosslinker of structure (d) of Group I is preferably attached to the 4-naphthyl position. It has been found that immunogens of the invention raise antibodies that are able to bind to several JWH molecules and metabolites. The skilled person is aware that for these antibodies to recognize JWH and CP molecules they must bind to particular structures or epitopes of the hapten (in this context the hapten being that part of the immunogen that is not the crosslinker or accm); the epitopes are often distinct groups incorporating functional groups. For example, with reference to the JWH immunogen of structure (a) of Group I, the epitope recognized by the antibody will be all or part of the 3-(1-naphthoyl)-1H-indole moiety, and for an immunogen of structure (b) of Group I the epitope recognized by the antibody will be all or part of the N-pentyl-3-carbonyl-1H-indole moiety. The accm can be any material that makes all or part of the hapten susceptible to antibody recognition and binding. For example the accm can be a protein, a protein fragment, a synthetic polypeptide or a semi-synthetic polypeptide. Especially preferred immunogens of the invention correspond to structures (a) and (c) of Group I in which structure (a) has Y=carbonyl, n=0 and D=pentylene and structure (c) has Y=carbonyl, A=O, n=1 and D=methylene.

Figure 6:
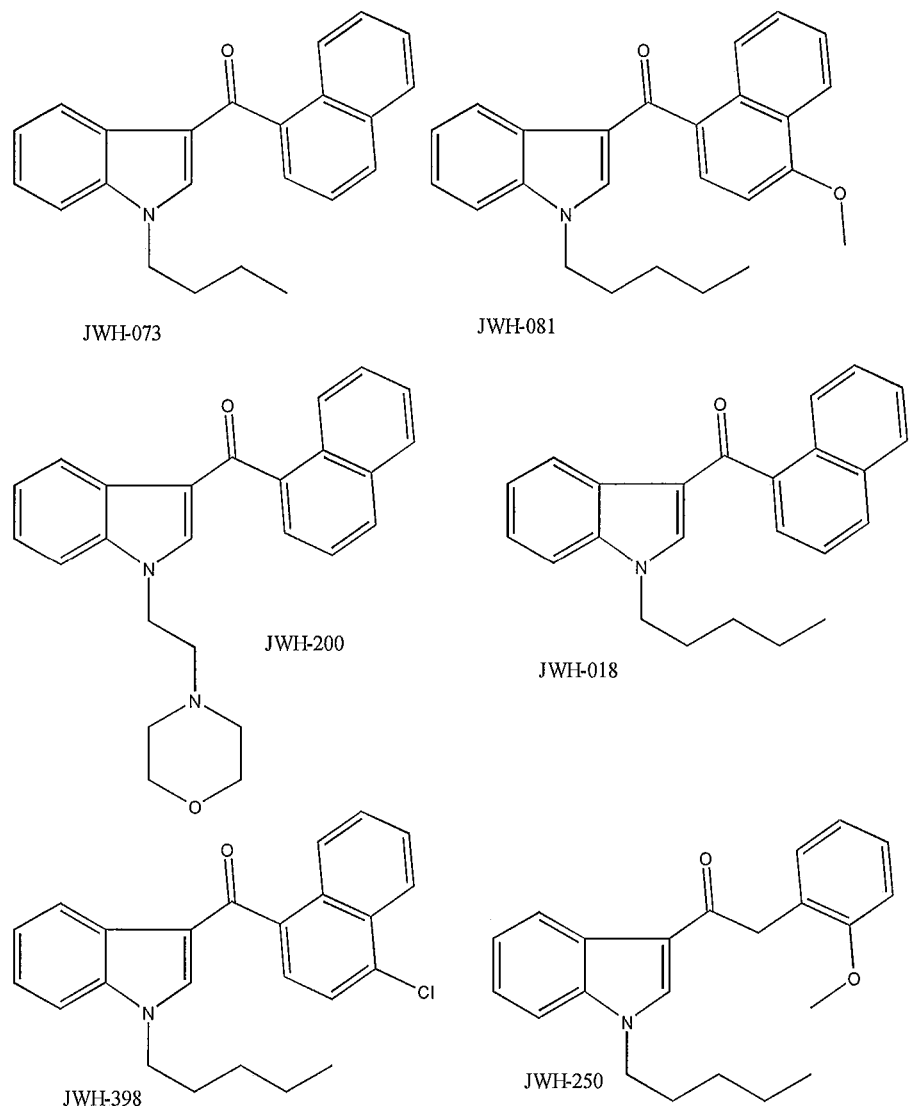
FIG. 6 is an illustration of representative molecules of the JWH family.
Figure 7:
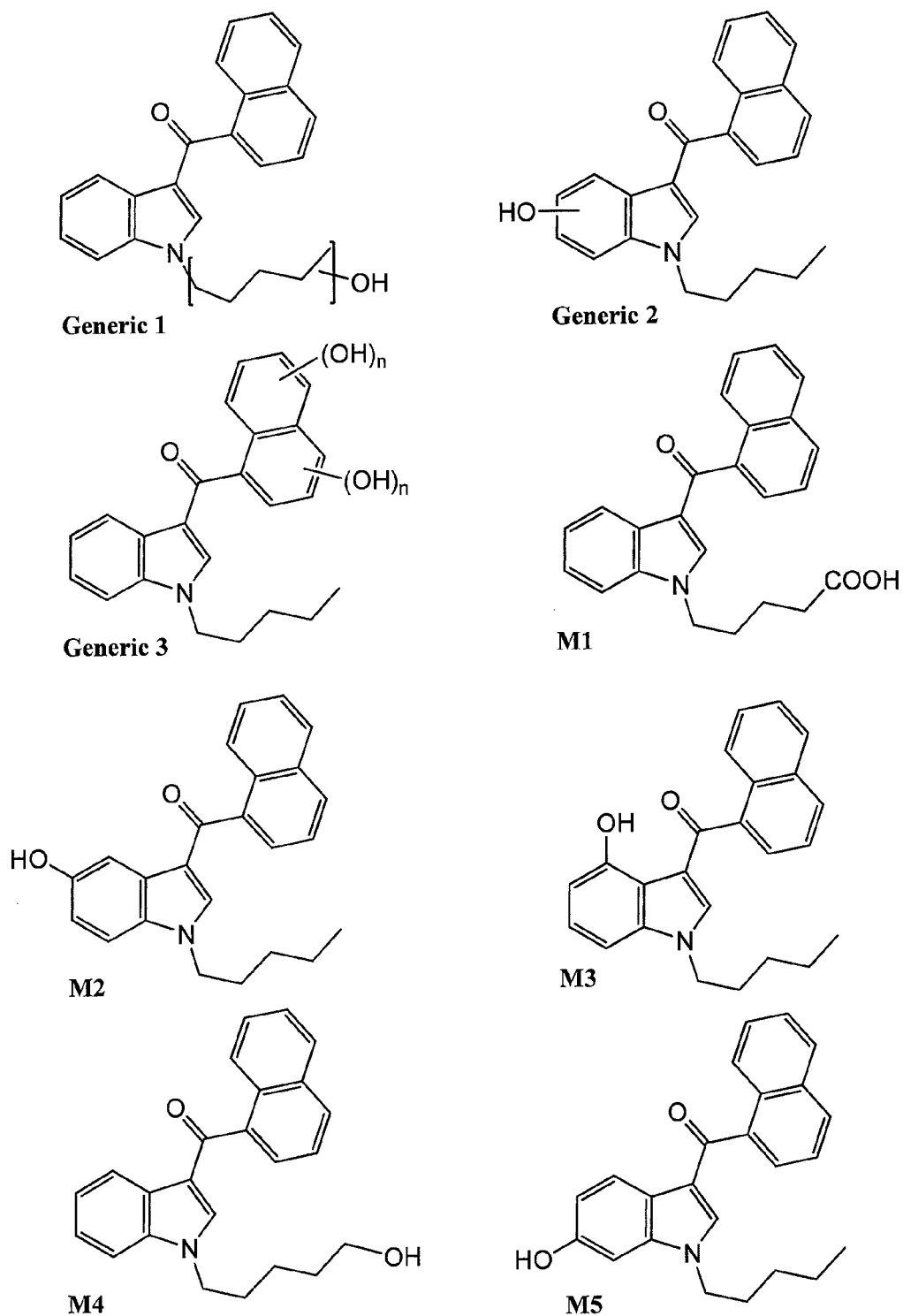
FIG. 7 is an illustration of identified and hypothesised metabolites of JWH (n=1-2). The hydroxylated metabolites are potentially further metabolised to the corresponding glucuronide(s).
Figure 8:
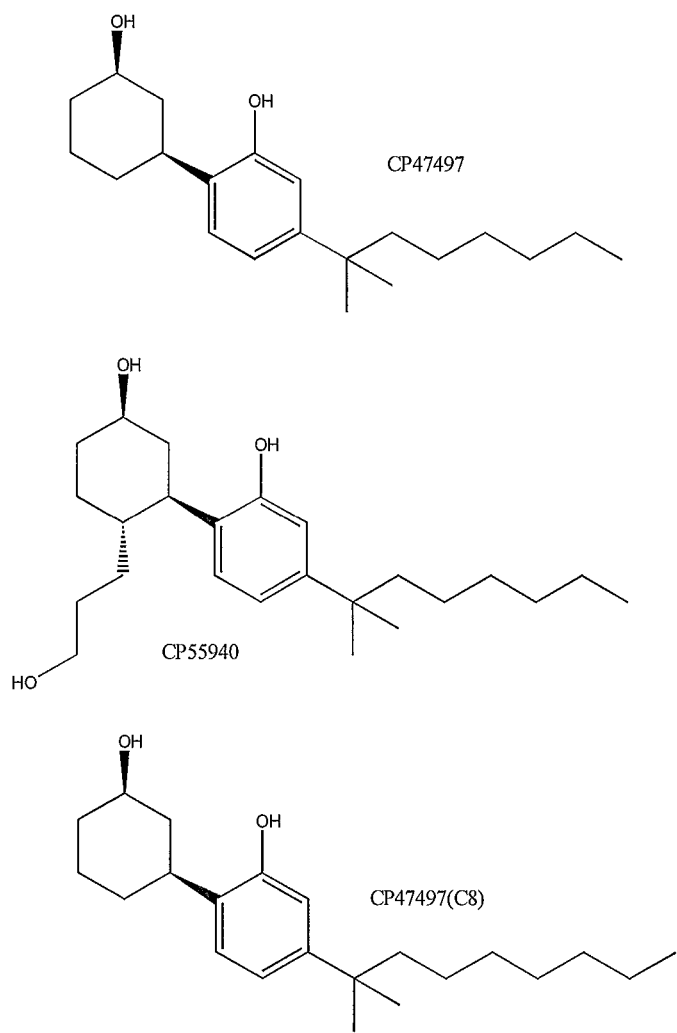
FIG. 8 is an illustration of CB1-active molecules of the CP family (available from Cayman Chemical company, 1180 East Ellsworth Road, Ann Arbor, Mich. 48108, USA).

A further aspect of the invention is an antibody raised against an immunogen of structure (a), (b) or (c) of Group I, that is able to bind to molecules of the JWH family and their metabolites that comprise structure I. The term 'able to bind to', as used herein, does not imply that the antibodies have a choice of whether or not to bind to the JWH molecules, but that under standard immunoassay conditions the antibodies will bind to the JWH or CP molecules. The antibodies are preferably raised against immunogens of structure (a) or (c) of Group I, the antibodies being able to bind to several molecules and metabolites of the JWH family, including JWH-018 and its N-alkyl hydroxylated metabolites. It is especially preferred that the antibodies are raised from structure (a) of Group I in which Y=carbonyl, n=0 and D=pentylene and structure (c) of Group I in which Y=carbonyl, A=O, n=1 and D=methylene, the antibodies able to bind to several molecules and metabolites of the JWH family, including JWH-018 and its dealkylated, hydroxylated and carboxylated metabolites, JWH-073, JWH-081, JWH-200 and JWH-398. Preferably, the antibodies raised against immunogens of structure (a) or (c) of Group I are also able to bind to one or more metabolites of JWH-018 identified as M1-M5 in FIG. 7, namely JWH-018 N-pentanoic acid metabolite (M1), JWH-018 5-hydroxyindole metabolite (M2), JWH-018 4-hydroxyindole metabolite (M3), JWH-018 N-(5-hydroxypentyl)metabolite (M4) and JWH-018 6-hydroxyindole metabolite (M5); and/or the JWH-018 metabolite JWH-018 N-(4-hydroxypentyl)metabolite; and/or the 5-fluoropentyl derivative of JWH-018, 1-(5-fluoropentyl)indol-3-yl (1-naphthyl) methanone; and/or the JWH-018 metabolite identified as JWH-250 in FIG. 6; and/or one or more JWH-073 metabolites selected from JWH-073 N-(3-hydroxybutyl) metabolite and JWH-073 N-(4-hydroxybutyl) metabolite. These compounds are available from, for example, Cayman Chemical Company. The antibodies also have the potential to bind to CB1-active derivatives of JWH molecules that could represent future generations of SSCs.

Optionally, the antibodies may have broad cross-reactivity across the JWH family and metabolites. For example, without intending to limit the invention thereto, antibodies raised to Immunogen I (structure (a) of Group I) may be specific to JWH-018 N-(5-hydroxypentyl)metabolite (M4) and cross-reactive to JWH-073, JWH-200, JWH-018, JWH-018 N-pentanoic acid metabolite (M1), JWH-018 5-hydroxyindole metabolite (M2), JWH-018 4-hydroxyindole metabolite (M3), JWH-018 6-hydroxyindole metabolite (M5) and 3-(1-naphthoyl)-1H-Indole. Similarly, antibodies raised to Immunogen II (structure (c) of Group I) may be specific to JWH-018 6-hydroxyindole metabolite (M5) and cross-reactive to JWH-073, JWH-200, JWH-398, JWH-018, JWH-018 N-pentanoic acid metabolite (M1), JWH-018 5-hydroxyindole metabolite (M2), JWH-018 4-hydroxyindole metabolite (M3) and JWH-018 N-(5-hydroxypentyl)metabolite (M4).

Optionally, the antibodies raised to Immunogen I (structure (a) of Group I) will be able to bind to an epitope of JWH-073, JWH-200, JWH-018, JWH-018 N-pentanoic acid metabolite (M1), JWH-018 5-hydroxyindole metabolite (M2), JWH-018 4-hydroxyindole metabolite (M3), JWH-018 N-(5-hydroxypentyl)metabolite (M4) and JWH-018 6-hydroxyindole metabolite (M5). Optionally, the epitope will be all or part of 341-naphthoyl)-1H-Indole. Further optionally, the antibodies raised to Immunogen II (structure (c) of Group I) will be able to bind to an epitope of JWH-073, JWH-200, JWH-398, JWH-018, JWH-018 N-pentanoic acid metabolite (M1), JWH-018 5-hydroxyindole metabolite (M2), JWH-018 4-hydroxyindole metabolite (M3), JWH-018 N-(5-hydroxypentyl) metabolite (M4) and JWH-018 6-hydroxyindole metabolite (M5).

The invention also describes an antibody raised against an immunogen of structure (d), (e), (f) or (g) the antibody being able to bind to molecules of the CP family, metabolites of CP molecules and future SSC molecules comprising structure II. When used in reference to an antibody, the word specific in the context of the current invention refers to the analyte that is preferably bound by the antibody, as gauged by a suitable metric such as the IC50. Given the IC50 of various analytes their cross-reactivities can be calculated. The antibody can either be a polyclonal or monoclonal antibody using well-known methods. If the polyclonal antibody possesses the required specificity and sensitivity, that is, it binds a single analyte within the detection range of the assay, development of a monoclonal antibody is unnecessary. Alternatively, a polyclonal or monoclonal antibody that binds to several analytes might be desirable; in the context of the current invention antibodies that bind several analytes are preferred. One or more antibodies of the invention can be incorporated into a kit for the detection and determination of individual or multiple SSCs. The skilled person in the immunodiagnostic field is aware of several alternative immunoassay formats that could incorporate the antibodies of the invention either in solution or tethered (e.g. covalently bonded or electrostatically 'non-bonded' through van der waal's forces) to a solid substrate such as beads, glass/plastic slides or ceramic chips (a chip defined as a small, planar substrate). A preferred solid substrate onto which the antibodies of the invention are covalently bonded is a chip, preferably a ceramic chip; the word 'biochip' can be used to refer to a chip with antibodies attached. Thus the invention also provides a solid substrate, preferably a biochip, comprising antibodies raised to an immunogen of one or more of structures (a), (b), (c), (d), (e), (f), (g) or (h), the antibodies being able to bind to an epitope of one or more molecules of the JWH family and/or CP family and/or one or more metabolites thereof. The antibodies of the invention can be used for the detection or determination of a single SSC such as JWH-018, either as the parent molecule or as a metabolite, but a preferred embodiment is the use of one or more antibodies, preferably two or more antibodies, at least one derived from Group I and one derived from Group II, for the detection or determination of several SSCs and/or their metabolites from the JWH and CP families. The detection and determination criteria for a SSC using an immunoassay platform includes, as is well-known in the art, exceeding a pre-defined cut-off/concentration value or measuring the calibrator equivalent value as derived from a calibrator curve (also referred to as a standard curve).

Another aspect of the invention is a method of detecting or determining synthetic cannabinoids of the JWH and/or CP families and their metabolites in an in vitro sample of an individual or in a solution derived from a substance suspected of containing synthetic cannabinoids comprising: contacting the sample or solution with one or more detecting agents and one or more antibodies of the invention that bind to molecules of the JWH family and/or one or more antibodies of the invention that bind to molecules of the CP family, measuring the detecting agents, and detecting or determining, by reference to calibrators, the presence or concentration of a molecule or molecules of the JWH family and/or CP family. With reference to 'detecting or determining', 'detecting' means qualitatively analyzing for the presence or absence of a substance, 'determining' means quantitatively analyzing for the amount of a substance. The detecting agent is a small molecule, generally of similar structure to a molecule to be detected conjugated to a labelling agent, that is able to bind to one of the antibodies of the invention. The labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material. For the purposes of the invention, the patient sample to be used for in vitro analysis can be hair or a peripheral biological fluid but is preferably whole blood, serum, plasma, or urine.

Preferably the synthetic cannabinoids to be detected or determined are one or more of JWH-018, JWH-073, JWH-200 and JWH-398 and the one or more antibodies are derived from immunogens of structures (a) and (c) of Group I. When referring to the detection or determination of a JWH or CP molecule, with or without a suffixed number attached to JWH and CP, the metabolite or metabolites are also inferred unless otherwise stated. The immunogen of structure (a) preferably has a crosslinker —X—Y— in which Y is carbonyl and is attached to the accm, and X is pentylene, and the immunogen of structure (c) has a crosslinker —O—CH2-C(O)— in which the carbonyl is attached to the accm.

Figure 5:
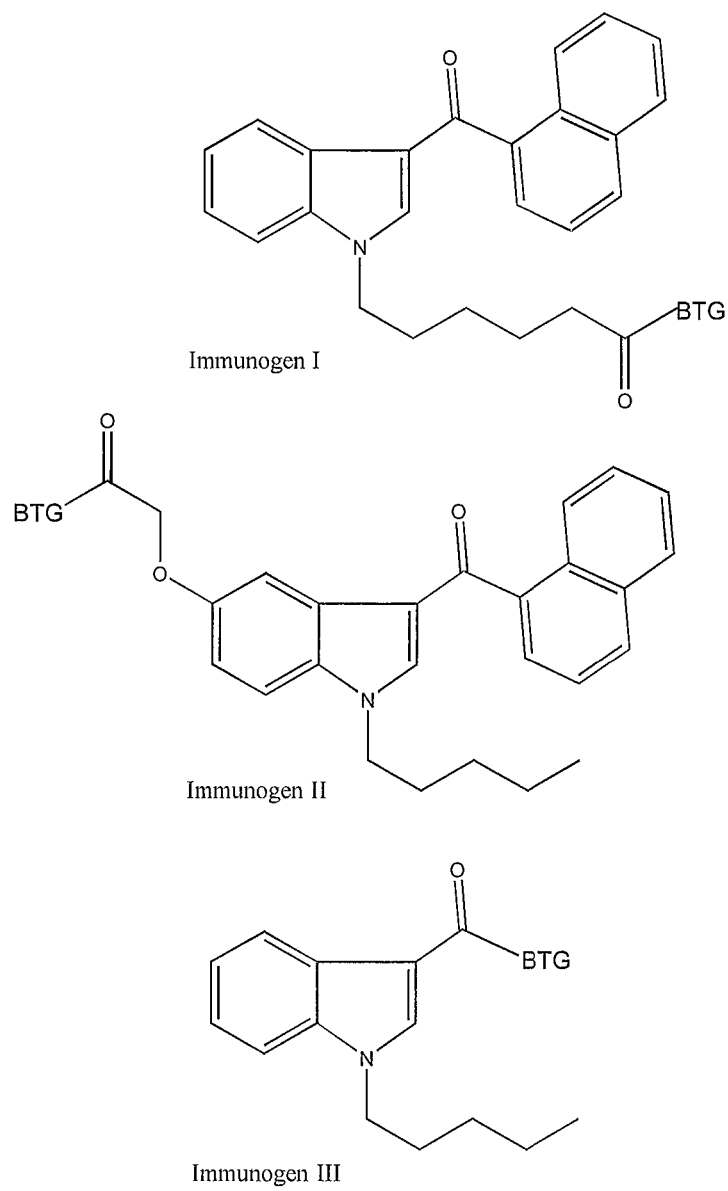
FIG. 5 is an illustration of Immunogens I, II and III.

The invention also describes kits for detecting or determining a molecule or molecules of the JWH family and/or CP family comprising one or more antibodies of the invention. Preferably, the kit comprises one or more antibodies raised to an immunogen of either structure (a), (b), (c) or (d) of Group I and one or more antibodies raised to an immunogen of structure (d), (e), (l) or (g) of Group II. More preferably the antibodies of the kit are derived from an immunogen of structure (a) and/or (c). A kit comprising antibodies derived from Immunogens I or II (FIG. 5) for detecting or determining one or more of JWH-018, JWH-073, JWH-200 and JWH-398 is particularly preferred. Optionally, the kit may comprise antibodies derived from Immunogens I or II for additionally or alternatively detecting or determining one of more of JWH-081, JWH-018 N-pentanoic acid metabolite (M1), JWH-018 5-hydroxyindole metabolite (M2), JWH-018 4-hydroxyindole metabolite (M3), JWH-018 N-(5-hydroxypentyl)metabolite (M4), JWH-018 6-hydroxyindole metabolite (M5), JWH-018 N-(4-hydroxypentyl)metabolite, 1-(5-fluoropentyl)indol-3-yl (1-naphthyl)methanone, JWH-250, JWH-073 N-(3-hydroxybutyl)metabolite and JWH-073 N-(4-hydroxybutyl)metabolite.

The antibodies of the kit are preferably tethered to any suitable solid support such as a chip. Although the solid support can be of any suitable shape such as a bead or a slide and of any suitable material such as silicon, glass or plastic, the solid support is preferably a ceramic chip. The kit may further include calibrators and one or more detecting agents and optionally includes instructions for the use of the antibodies of the kit and if incorporated, the calibrators and detecting agents, for detecting and determining molecules from the JWH and/or CP families. The invention also embodies solid supports comprising the novel antibodies.

The antibodies of the invention are used for the detection or determination of JWH and/or CP molecules either in herbal mixtures, an in vitro sample taken from an individual or any other substance suspected of their incorporation. A preferred use of the antibodies of the invention is their use in the detection and/or quantification of JWH-018, JWH-073, JWH-200 and JWH-398 in herbal mixtures and/or JWH-073, JWH-200, JWH-398 and JWH-018 and its metabolites in in vitro samples taken from individuals.

General Methods, Examples and Results

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 μl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Example—1

Preparation of 3-(1-naphthoyl)-1H-indole 1

To a cooled solution of indole (5.85 g, 50 mmol) in ether (50 ml) under nitrogen was added slowly a solution of methylmagnesium bromide (3M) in ether (17.5 ml). After addition, the reaction mixture was warmed up to room temperature and stirred for 2 h at room temperature. Then the mixture was cooled down again to 0° C., and to it was added slowly with stirring a solution of 1-naphthoylchloride (9.5 g, 50 mmol) in ether (50 ml). The resulting mixture was warmed up to room temperature and stirred for 2 h at room temperature followed by slow addition of saturated ammonium chloride solution (375 ml). The mixture was then stirred overnight at room temperature. A white solid was formed, filtered, washed by ether and dried under high vacuum to give 3-(1-naphthoyl)-1H-Indole 1 (12.3 g, 91%).

Example—2

Preparation of N-(5-Ethoxycarbonylpentyl)-3-(1-naphthoyl)-1H-indole 2

To a suspension of sodium hydride (1.1 g, 30 mmol, 60% in mineral oil) in DMF (100 ml) under nitrogen was added solid 3-(1-naphthoyl)-1H-indole 1 (5.43 g, 20 mmol). After stirring at room temperature for 1 h, a solution of ethyl 6-bromohexanoate (6.6 g, 30 mmol) in DMF (10 ml) was added slowly with stirring over a period of 15 min and the mixture was then heated at 60° C. for 3 h. The solvent was removed under high vacuum and the crude product was suspended in water (150 ml) and extracted by ethyl acetate (2×150 ml). The combined ethyl acetate phases were washed by water (1×100 ml), brine (1×100 ml), dried over sodium sulphate filtered and concentrated to dryness. The crude product obtained was purified by chromatography on silica gel using hexane/ethyl acetate (8/2) to give the title compound 2 as an oil which became solid in the cold (7.1 g, 86%).

Example—3

Preparation of N-(5-carboxypentyl)-3-(1-naphthoyl)-1H-indole (Hapten-A)

To a solution of 2 (5.0 g, 12 mmol) in a mixture of THF/H2O (1:1) was added potassium hydroxide (1.7 g) and the mixture was stirred at 60° C. for 1 h. The THF was removed under vacuum, the aqueous solution acidified to pH 1 by the addition of hydrochloric acid solution (1N) and extracted by ethyl acetate (3×100 ml). The combined organic phases were washed by water (100 ml), brine solution (100 ml), dried over sodium sulphate, filtered and concentrated to dryness. The crude product obtained was dissolved in ethyl acetate (10 ml) and the Hapten-A precipitated by the addition of a mixture of ether/hexane as a white solid, filtered and dried under high vacuum to give Hapten-A (3.6 g, 78%).

Example—4

Conjugation of Hapten-A to BSA

To a solution of Hapten-A (52.2 mg, 0.13 mmol) in DMF (1.0 ml) was added N,N-dicyclohexylcarbodiimide (DCC) (34.0 mg, 0.16 mmol) and N-hydroxysuccinimide (19.0 mg, 0.16 mmol) and the mixture was stirred at room temperature overnight. The dicyclohexylurea formed was removed by filtration and the solution added dropwise to a solution of BSA (200 mg, 3.0 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried. MALDI results showed 9.83 molecule of Hapten-A had been conjugated to one molecule of BSA.

Example—5

Conjugation of Hapten-A to BTG (Immunogen I)

To a solution of Hapten-A (58.0 mg, 0.15 mmol) in DMF (1.0 ml) was added N,N-dicyclohexylcarbodiimide (DCC) (34.0 mg, 0.165 mmol) and N-hydroxysuccinimide (19.0 mg, 0.16 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried to give Immunogen I.

Example—6

Conjugation of Hapten-A to HRP

EDC hydrochloride (10 mg) was dissolved in water (0.5 ml) and immediately added to a solution of Hapten-A (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP detecting agent was then dialysed overnight against 10 L of PBS at pH 7.2 at 4° C.

Example—7

Preparation of 5-methoxy-3-(1-naphthoyl)-1H-indole 4

To a cooled solution at 0° C. of 5-methoxy-1H-indole 3 (7.4 g, 50 mmol) in diethyl ether (150 ml) under nitrogen was added dropwise a solution of methylmagnesium bromide (3M) in diethyl ether (17.5 ml) and the mixture was stirred for 2 h at room temperature. The solution was then cooled at 0° C. and to this solution was added a solution of 1-naphthoylthloride (9.5 g, 50 mmol) in diethyl ether (100 ml) dropwise over a period of 15 min. After the addition was completed the solution was warmed up at room temperature and stirred for 2 h followed by slow addition of saturated ammonium chloride solution (375 ml) and stirred overnight. The white solid formed was filtered, washed by ether and dried under high vacuum to give 5-methoxy-3-(1-naphthoyl)-1H-indole 4 (11.3 g, 75%).

Example—8

Preparation of 5-methoxy-3-(1-naphthoyl)-N-pentyl-1H-indole 5

To a suspension of sodium hydride (1.54 g, 45.7 mmol, 60% in mineral oil) in DMF (100 ml) under nitrogen was added dropwise a solution of 5-methoxy-3-(1-naphthoyl)-1H-indole 4 (9.83 g, 32.6 mmol) in DMF (50 ml) and the mixture was stirred at 40° C. for 1 h. The solution was then cooled to room temperature and to this mixture was added a solution of 1-bromopentane (8.2 g, 54.3 mmol) in DMF (25 ml). The mixture was stirred at 60° C. for 1 h. The solvent was removed under high vacuum and the crude product was suspended in water (200 ml) and extracted by ethyl acetate (2×200 ml). The combined ethyl acetate phases were washed by water (1×100 ml), brine (1×100 ml), dried over sodium sulphate, filtered and concentrated to dryness. The crude product obtained was purified by chromatography on silica gel using hexane/ethyl acetate (7/3) to give the title compound 5 as an oil which solidified upon cooling (7.1 g, 59%).

Example—9

Preparation of 5-hydroxy-3-(1-naphthoyl)-N-pentyl-1H-indole 6

To a solution of hydrobromic acid (48 w/w %) in water (150 ml) was added 5 (6.5 g, 17.5 mmol) and the mixture was heated at reflux for 3 h. The solution was cooled to room temperature and concentrated to dryness. Water was then added (200 ml), the solution neutralized to pH 7-8 and then extracted with ethyl acetate (3×150 ml). The combined organic layers were washed by water (150 ml), brine (150 ml), dried over $Na_2SO_4$, filtered and concentrated to dryness. The crude product was then recrystallized from ethyl acetate/hexane to give a white solid of 5-hydroxy-3-(1-naphthoyl)-N-pentyl-1H-indole 6 (4.5 g, 72%)

Example—10

Preparation of 5-(tert-butoxycarbonylmethoxy)-3-(1-naphthoyl)-N-pentyl-1H-indole 7

To a suspension of sodium hydride (452 mg, 13.4 mmol, 60% in mineral oil) in DMF (25 ml) under nitrogen was added dropwise a solution of 6 (3.7 g, 10.35 mmol) in DMF (50 ml) and the mixture was stirred at 60° C. for 1 h. The solution was then cooled to room temperature and to this mixture was added a solution of tert-butyl bromoacetate (2.62 g, 13.4 mmol) in DMF (25 ml). The mixture was stirred at 60° C. for 3 h. The DMF was removed under high vacuum and the crude product was suspended in water (100 ml) and the mixture was extracted by ethyl acetate (2×100 ml). The combined ethyl acetate phases were washed by water (1×50 ml), brine (1×50 ml), dried over sodium sulphate filtered and concentrated to dryness. The crude product obtained was purified by chromatography on silica gel using hexane/ethyl acetate (9/1) to give the title compound 7 (3.5 g, 72%).

Example—11

Preparation of 5-carboxymethoxy-3-(1-naphthoyl)-N-pentyl-1H-indole (Hapten-B)

To a solution of 7 (3.0 g, 6.4 mmol) in dichloromethane (50 ml) was added TFA (25 ml) and the mixture was stirred at room temperature for 3 h. The mixture was evaporated to dryness and the crude obtained was purified by chromatography on silica-gel using 5% methanol in chloroform to give Hapten-B (2.1 g, 79%).

NMR $^{13}C$ ($CD_3OD$, δ ppm): 194.55, 173.21, 156.53, 141.14, 140.15, 135.25, 134.10, 131.98, 131.17, 129.46, 128.9, 1127.85, 127.44, 126.87, 125.55, 125.85, 117.92, 115.14, 112.72, 106.33, 65.54, 30.59, 29.87, 23.2, 14.25

Example—12

Conjugation of Hapten-B to BSA

To a solution of Hapten-B (62.4 mg, 0.15 mmol) DMF (1.0 ml) was added N,N-dicyclohexylcarbodiimide (DCC) (34.1 mg, 0.16 mmol) and N-hydroxysuccinimide (19.02 mg, 0.16 mmol) and the mixture was stirred at room temperature overnight. The dicyclohexylurea formed was removed by filtration and the solution was added dropwise to a solution of BSA (200 mg, 3 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried. MALDI results showed 37.2 molecules of Hapten-B had been conjugated to one molecule of BSA.

Example—13

Conjugation of Hapten-B to BTG (Immunogen II)

To a solution of Hapten-B (56.0 mg, 0.13 mmol) in DMF (1.0 ml) was added N,N-dicyclohexylcarbodiimide (DCC)

(30.6 mg, 0.14 mmol) and N-hydroxysuccinimide (17.1 mg, 0.14 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (15 ml). The mixture was then stirred overnight at 4° C. The solution was then dialysed against 50 mM phosphate buffer pH 7.2 (3 changes) for 24 h at 4° C., and freeze-dried to give Immunogen II.

Example—14

Preparation of 3-carboxy-1-pentyl-1H-indole (Hapten-C)

Indole 3-carboxylic acid (3 g, 18.62 mmol) was added to a suspension of sodium hydride (60% in oil) (1.11 g, 1.5 eq) in dry DMF (30 ml) under a nitrogen atmosphere. The mixture was stirred at room temperature for 45 min (H2 evolving has ceased) and to this was added 1-bromopentane (4.62 ml, 2 eq) in dry DMF (10 ml) dropwise. The mixture was stirred at room temperature overnight. The solvents were removed in vacuo and to the residue was added water (30 ml) and ethyl acetate (30 ml). The ethyl acetate portion was separated, dried over sodium sulphate, filtered and evaporated to dryness. The crude residue was purified by column chromatography (silica gel: 20% ethyl acetate in hexane) to give the title compound (2.12 g, 49%) as a cream solid.

Example—15

Conjugation of 3-carboxy-1-pentyl-1H-indole (Hapten C) to BSA

To a solution of Hapten-C (26.13 mg, 0.113 mmol) in DMF (1.0 ml) was added N,N-dicyclohexylcarbodiimide (DCC) (25.64, 0.1243 mmol) and N-hydroxysuccinimide (14.30 mg, 0.1243 mmol) and the mixture was stirred at room temperature overnight. The dicyclohexylurea formed was removed by filtration and the solution was added dropwise to a solution of BSA (150 mg) in 100 mM sodium bicarbonate solution (pH 8.5) (9 ml). The mixture was then stirred overnight at 4° C. The solution was then dialysed against 50 mM phosphate buffer pH 7.2 (3 changes) for 24 hours at 4° C., and freeze-dried.

Example—16

Conjugation of 1-pentyl-1-H-indole-3-carboxylic acid (3-carboxy-1-pentyl-1H-indole, Hapten C) to BTG (Immunogen III)

To a solution of Hapten-C (31.22 mg, 0.135 mmol) in DMF (1.0 ml) was added N,N-dicyclohexylcarbodiimide (DCC) (30.74 mg, 0.149 mmol) and N-hydroxysuccinimide (17.1 mg, 0.149 mmol) and the mixture was stirred at room temperature overnight. The dicyclohexylurea formed was removed by filtration and the solution was added dropwise to a solution of BTG (150 mg) in 100 mM sodium bicarbonate solution (pH 8.5) (15 ml). The mixture was then stirred overnight at 4° C. The solution was then dialysed against 50 mM phosphate buffer pH 7.2 (3 changes) for 24 hours at 4° C., and freeze-dried to give Immunogen III.

Example—17

Conjugation of Hapten-B to HRP

EDC hydrochloride (10 mg) was dissolved in water (0.5 ml) and immediately added to a solution of Hapten-B (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP detecting agent was then dialysed overnight against 10 L of PBS at pH 7.2 at 4° C.

Example 18

Preparation of antibodies to Immunogens I and II

Aqueous solutions of the immunogens prepared in examples 5 and 13 were formulated with Freund's Complete Adjuvant (FCA) to form emulsions consisting of 2 mg/ml Immunogen 1 and 2 mg/ml of Immunogen II in 50% (v/v) FCA. Three sheep were immunised with each emulsion (1° immunisations), 0.25 ml being intramuscularly injected at four sites in the rump of each animal. Subsequent immunisations (boosts 2-8) contained 1 mg/ml Immunogen I and 1 mg/ml Immunogen II. All boosts were emulsified in 50% (v/v) Freund's Incomplete Adjuvant (FIA) and administered to the appropriate sheep in the same manner as the 1° immunisations, at monthly intervals. Blood sampling took place 7-14 days after each boost. Each sample was processed to produce antiserum, which was further purified by caprylic acid and ammonium sulphate precipitation to yield an immunoglobulin (Ig) fraction. The Ig fraction was evaluated by competitive ELISA microtiter plate assay, as described in example 19 below.

Example 19

Development of Competitive ELISA for JWH Synthetic Cannabinoids and Metabolites (a) The wells of an enhanced binding 96 well polystyrene microtiter plate were coated with the Ig fraction of the antiserum raised to Immunogen II (Hapten B-BTG—example 13) and diluted in 10 mM Tris, pH 8.5 (125 µl/well). The appropriate antibody coating concentration was determined using standard ELISA checkerboard techniques. The plate was incubated for 2 hours at 37° C., washed 4 times over a 10-minute period with Tris buffered saline containing Tween 20 (TBST) and tapped dry. Standard solutions of JWH synthetic cannabinoids, metabolites and selected molecules were prepared in TBST and 50 µl of each, was added to the appropriate wells. 75 µl of conjugate (Hapten A-HRP) diluted in Tris buffer containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. The excess unbound conjugate was removed by washing 6 times over a 10-minute period with TBST and tapped dry. 125 µl of tetramethylbenzedine (TMB) substrate solution was added to each well of the plate that was then incubated for 15-20 minutes in the dark at room temperature. The reaction was terminated by addition of 125 µl of 0.2M sulphuric acid to each well. The absorbance was then measured at 450 nm using a microtiter plate reader.

Employing each series of standards, calibration curves were generated and these were used to determine the specificity of the immunoassay for the JWH synthetic cannabinoids, metabolites and selected molecules. The results of this study are presented in Tables 1 to 3, cross-reactivity being calculated according to the following formula:

% CR=$IC_{50,JWH-018}/IC_{50,CR} \times 100$

Where % CR is the percentage cross-reactivity, IC50, JWH-018 is the concentration of JWH-018 that causes 50% displacement of signal and IC50, CR is the concentration of JWH synthetic cannabinoid/metabolite/selected molecule that causes 50% displacement of signal.

Table 1: Data generated from a competitive microtiter plate assay for JWH synthetic cannabinoids and metabolites, employing antiserum raised to Immunogen II (Hapten B-BTG) and conjugate (Hapten A-HRP) as detection reagent.

(b) In a similar manner to that described in Example 19(a), the wells of a 96 well microtiter plate were coated with the Ig fraction of the antiserum raised to Immunogen I (Hapten A-BTG—example 5). Conjugate (Hapten A-HRP) was employed as a detection reagent. The data generated is presented in Table 2.

Table 2: Data generated from a competitive microtiter plate assay for JWH synthetic cannabinoids and metabolites, employing antiserum raised to Immunogen I (Hapten A-BTG) and conjugate (Hapten A-HRP) as detection reagent.

(c) The resulting competitive ELISA for synthetic cannabinoids and metabolites was further employed to analyse urine and serum samples from 20 patients (Table 3).

(d) The resulting competitive ELISA for synthetic cannabinoids and metabolites was also employed to test for the 5-fluoropentyl derivative of JWH-018, (1-(5-fluoropentyl) indol-3yl (1-naphthyl)methanone (Table 4).

Results

TABLE 1

Antibody characterisation using antiserum raised to Immunogen II and detecting agent derived from Hapten-A in a competitive assay format (CR based on 100% for JWH-018)

| Analyte | $IC_{50}$ ng/ml | % Cross-reactivity |
| --- | --- | --- |
| JWH-018 | 2.11 | 100.00 |
| JWH-073 | 1.56 | 135.26 |
| JWH-398 | 17.55 | 12.02 |
| JWH-200 | 1.66 | 127.11 |
| 3-(1-naphthoyl)-1H-Indole | >>40 | <<5.28 |
| M1 | 5.48 | 38.50 |
| M2 | 1.62 | 130.25 |
| M3 | 9.16 | 23.03 |
| M4 | 1.15 | 183.48 |
| M5 | 0.98 | 215.31 |

>> implies a value greatly exceeding the value given (40 ng/ml was the highest concentration tested)
<< implies a value greatly below the value given

TABLE 2

Antibody characterisation using antiserum raised to Immunogen I and detecting agent derived from Hapten-A in a competitive assay format (CR based on 100% for JWH-018)

| Analyte | $IC_{50}$ ng/ml | % Cross-reactivity |
| --- | --- | --- |
| JWH-018 | 2.71 | 100.00 |
| JWH-073 | 0.93 | 291.40 |
| JWH-398 | >>40 | <<6.78 |
| JWH-200 | 0.31 | 874.19 |
| 3-(1-naphthoyl)-1H-Indole | 3.84 | 70.57 |
| M1 | 0.42 | 645.24 |
| M2 | 0.39 | 694.87 |
| M3 | 25.51 | 10.62 |
| M4 | 0.18 | 1505.56 |
| M5 | 2.04 | 132.84 |

>> implies a value greatly exceeding the value given (40 ng/ml was the highest concentration tested)
<< implies a value greatly below the value given

TABLE 3

Sensitivity and cross-reactivity (CR) of antibodies raised to Immunogens I & II of selected molecules

| Analyte | Standard Conc$^n$ ng/ml | $IC_{50}$ ng/ml | % CR |
| --- | --- | --- | --- |
| Serotonin | 750.00 | >750.00 | <0.28 |
| 4-Methoxypsilocin | 750.00 | >750.00 | <0.28 |
| Delta-9-THC | 750.00 | >750.00 | <0.28 |
| Cannabinol | 750.00 | >750.00 | <0.28 |
| 11-Hydroxy-δ-9-THC | 750.00 | >750.00 | <0.28 |
| CP 47,497 | 750.00 | >750.00 | <0.28 |
| 3-Carboxy-N-pentyl-1H-indole | 750.00 | >750.00 | <0.28 |
| 3-Carboxy-1H-indole | 750.00 | >750.00 | <0.28 |
| 3-Carboxymethyl-5-hydroxy-1H-indole | 750.00 | >750.00 | <0.28 |
| 5-Hydroxytryptophol | 750.00 | >750.00 | <0.28 |

TABLE 4

Sensitivity and cross-reactivity (CR) of antibodies raised to Immunogens I & II of JWH-018 and 1-(5-Fluoropentyl)indol-3-yl (1-naphthyl) methanone* (5-Fluoropentyl derivative)

| Immunogen | | $IC_{50}$ ng/ml | % Cross-reactivity |
| --- | --- | --- | --- |
| I | JWH-018 | 2.30 | 100.00 |
| I | 5-Fluoropentyl derivative | 0.02 | 11500.00 |
| II | JWH-018 | 1.97 | 100.00 |
| II | 5-Fluoropentyl derivative | 0.22 | 908.00 |

*Binding of this molecule to the $CB_1$ receptor is detailed in U.S. Pat. No. 6,900,236

Immunoassays using antibodies of the invention to test for potential cross-reactants (Table 3) and to screen the urine and serum of twenty patients for cross-reactive molecules, did not reveal any cross-reactants which could invalidate the measurements taken using the antibodies, methods, kits and products of the invention.

As can be seen from Tables 1 to 3, for the first time antibodies have been provided that bind to various JWH molecules, metabolites and potential metabolites, whereas other common indole-containing molecules and non-JWH CB1-active molecules do not bind. The antibody produced from Immunogen I is able to bind to JWH molecules known to be incorporated in herbal therapeutics such as JWH-018, proposed metabolites such as M2 (Wintermeyer et al 2010), and potential metabolites such as M5. The detection and quantification of other JWH SSCs is also provided for, the antibodies of the invention bind a range of molecules comprising the 3-(1-naphthoyl)-1H-indole structure (e.g. JWH-071, JWH-398, M1 etc.). Table 3 confirms that the same antibodies do not cross-react with other psychoactive drugs, with molecules present in biological samples of patients who have not taken JWH containing substances or with molecules without the 3-(1-naphthoyl)-1H-indole such as 3-carboxy-1H-indole. The concept of using the antibodies of the invention to detect and determine future stealth synthetic cannabinoids is highlighted in Table 4; the 5-fluoropentyl derivative known to bind the CB1 receptor, but which as of yet has not been detected in herbal therapeutics or similar substances, binds to antibodies raised from Immunogens I and II.

The invention claimed is:

1. An antibody raised to an immunogen of structure (a),

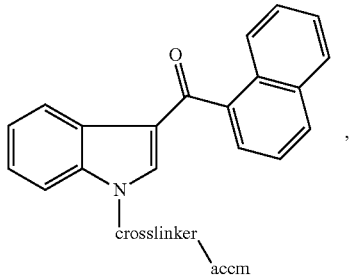

wherein
the crosslinker is —X—Y—, wherein X is linked to the N atom of the indole ring and Y is linked to the accm,
wherein Y is selected from the group consisting of carbonyl, amino, thio and azo, or Y is generated by reacting accm with X which is substituted with a terminal functional group selected from the group consisting of maleimide, isocyanate, isothiocyanate, aldehyde and dithiopyridine, and
wherein X is —(CO)$_n$-D-, wherein D is linked to Y, wherein
n=0 or 1, and
D is a C$_{1-10}$ substituted or unsubstituted straight chain alkylene or arylene moiety, and
wherein accm is an antigenicity conferring carrier material,
wherein the antibody has an average cross-reactivity, relative to JWH-018, of less than 0.28% to serotonin, 4-methoxypsilocin, δ-9-THC, cannabinol, 11-hydroxy-δ-9-THC, CP 47,497, 3-carboxy-N-pentyl-1H-indole, 3-carboxy-1H-indole, 3-carboxymethyl-5-hydroxy-1H-indole and 5-hydroxytryptophol; and,
wherein the antibody has an average cross-reactivity, relative to JWH-018, of at least 100% to JWH-073, JWH-200, JWH-018 N-pentanoic acid metabolite (M1), JWH-018 5-hydroxyindole metabolite (M2), JWH-018 N-(5-hydroxypentyl) metabolite (M4), JWH-018 6-hydroxyindole metabolite (M5), and 1-(5-fluoropentyl)indol-3-yl-(1-naphthyl)methanone; and
wherein the antibody has an average cross-reactivity, relative to JWH-018, of less than 6.78% to JWH-398.

2. The antibody of claim 1, wherein the antibody binds to 3-(1-naphthoyl)-1H-indole.

3. The antibody of claim 1, wherein Y=carbonyl, n=0 and D=1,5-pentylene.

4. The antibody of claim 1 having an IC$_{50}$ of greater than 750 ng/ml for serotonin, 4-methoxypsilocin, δ-9-THC, cannabinol, 11-hydroxy-δ-9-THC, CP 47,497, 3-carboxy-N-pentyl-1H-indole, 3-carboxy-1H-indole, 3-carboxymethyl-5-hydroxy-1H-indole and 5-hydroxytryptophol.

5. A method of detecting or determining synthetic cannabinoids of the JWH family, a metabolite thereof or a combination thereof in an in vitro sample of an individual or in a solution derived from a substance suspected of containing synthetic cannabinoids, the method comprising
contacting the sample or solution with at least one detecting agent and at least one antibody of claim 1;
detecting or determining the quantity of the at least one detecting agent; and
deducing from calibrators the presence of or amount of a molecule or molecules of the JWH family, the metabolite thereof or the combination thereof in the sample or solution.

6. The method of claim 5, wherein the synthetic cannabinoids to be detected or determined are selected from the group consisting of JWH-018, JWH-073 and JWH-200.

7. The method of claim 5, wherein the crosslinker is —X—Y— wherein Y is carbonyl and X is 1,5-pentylene.

8. A kit for detecting or determining at least one molecule of the JWH family, a metabolite thereof or a combination thereof, the kit comprising at least one antibody raised to the immunogen of structure (a):

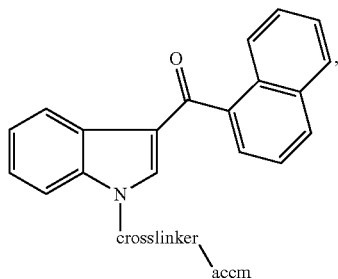

wherein:
the crosslinker is —X—Y—, wherein X is linked to the N atom of the indole ring and Y is linked to the accm,
wherein Y is selected from the group consisting of carbonyl, amino, thio and azo, or Y is generated by reacting accm with X which is substituted with a terminal functional group selected from the group consisting of maleimide, isocyanate, isothiocyanate, aldehyde and dithiopyridine, and
wherein X is —(CO)$_n$-D-, wherein D is linked to Y, wherein
n=0 or 1, and
D is a C$_{1-10}$ substituted or unsubstituted straight chain alkylene or arylene moiety, and
wherein accm is an antigenicity conferring carrier material,
wherein the antibody has an average cross-reactivity, relative to JWH-018, of less than 0.28% to serotonin, 4-methoxypsilocin, δ-9-THC, cannabinol, 11-hydroxy-δ-9-THC, CP 47,497, 3-carboxy-N-pentyl-1H-indole, 3-carboxy-1H-indole, 3-carboxymethyl-5-hydroxy-1H-indole and 5-hydroxytryptophol;
wherein the antibody has an average cross-reactivity, relative to JWH-018, of at least 100% to JWH-073, JWH-200, JWH-018 N-pentanoic acid metabolite (M1), JWH-018 5-hydroxyindole metabolite (M2), JWH-018 N-(5-hydroxypentyl) metabolite (M4), JWH-018 6-hydroxyindole metabolite (M5), and 1-(5-fluoropentyl)indol-3-yl-(1-naphthyl)methanone; and
wherein the antibody has an average cross-reactivity, relative to JWH-018, of less than 6.78% to JWH-398.

9. The kit of claim 8, wherein Y=carbonyl, n=0 and D=1,5-pentylene.

10. The kit of claim 8, wherein the antibody has an IC$_{50}$ of greater than 750 ng/ml for serotonin, 4-methoxypsilocin, δ-9-THC, cannabinol, 11-hydroxy-δ-9-THC, CP 47,497, 3-carboxy-N-pentyl-1H-indole, 3-carboxy-1H-indole, 3-carboxymethyl-5-hydroxy-1H-indole and 5-hydroxytryptophol.

11. The kit of claim 8, wherein the antibody binds to 3-(1-naphthoyl)-1H-indole.

\* \* \* \* \*